(12) United States Patent
Wohlschlager et al.

(10) Patent No.: US 12,237,876 B2
(45) Date of Patent: Feb. 25, 2025

(54) RECOMMENDING WHETHER A SUBJECT MONITORING SYSTEM USES A WIRELESS COMMUNICATION MODE

(71) Applicant: KONINKLIJKE PHILIPS N.V., Eindhoven (NL)

(72) Inventors: Markus Silvester Wohlschlager, Sindelfingen (DE); Hansjoerg Geywitz, Kusterdingen (DE); Daniel Gal, Boeblingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 537 days.

(21) Appl. No.: 17/438,107

(22) PCT Filed: Mar. 4, 2020

(86) PCT No.: PCT/EP2020/055610
§ 371 (c)(1),
(2) Date: Sep. 10, 2021

(87) PCT Pub. No.: WO2020/182553
PCT Pub. Date: Sep. 17, 2020

(65) Prior Publication Data
US 2022/0166529 A1    May 26, 2022

(30) Foreign Application Priority Data
Mar. 13, 2019   (EP) .................................... 19162555

(51) Int. Cl.
*H04B 17/318*    (2015.01)
*H04B 17/382*    (2015.01)
(Continued)

(52) U.S. Cl.
CPC ......... *H04B 17/382* (2015.01); *H04B 17/318* (2015.01); *H04Q 9/00* (2013.01);
(Continued)

(58) Field of Classification Search
None
See application file for complete search history.

(56) References Cited

U.S. PATENT DOCUMENTS 7,390,299 B2    6/2008  Colquitt
8,185,204 B2    5/2012  Bange
(Continued)

FOREIGN PATENT DOCUMENTS

CN    101605368 A    12/2009
CN    105142163 A    12/2015
(Continued)

OTHER PUBLICATIONS

International Search Report and Written Opinion, International Application No. PCT/EP2020/055610, Mailed on May 28, 2020.
(Continued)

*Primary Examiner* — Duc T Duong (57) ABSTRACT

A method and communications module for recommending in what manner or mode a sensor and communications module of a subject monitoring system should communicate. A determination is made as to whether or not more than a predetermined number of wireless channels have a noise level below a certain threshold. If a positive determination is made, a wireless communication mode is recommended. If a negative determination is made, a wireless communication mode is not recommended.

18 Claims, 3 Drawing Sheets

(51) Int. Cl.
*H04Q 9/00* (2006.01)
*H04W 40/12* (2009.01)
*A61B 5/00* (2006.01)
*A61B 5/024* (2006.01)

(52) U.S. Cl.
CPC ............ *A61B 5/0011* (2013.01); *A61B 5/002* (2013.01); *A61B 5/0024* (2013.01); *A61B 5/024* (2013.01); *H04Q 2209/30* (2013.01); *H04Q 2209/43* (2013.01)

(56) References Cited

U.S. PATENT DOCUMENTS

| | | | |
|---|---|---|---|
| 2007/0049983 A1 | 3/2007 | Freeberg | |
| 2010/0246469 A1* | 9/2010 | Gheorghiu | H04L 1/0026 370/312 |
| 2010/0316009 A1* | 12/2010 | Han | H04L 43/024 370/329 |
| 2012/0029315 A1 | 2/2012 | Raptis et al. | |
| 2013/0023214 A1 | 1/2013 | Wang | |
| 2013/0082598 A1* | 4/2013 | Csato | H05B 45/00 315/84 |
| 2016/0338617 A1* | 11/2016 | Ashe | A61B 5/7282 |
| 2017/0332243 A1* | 11/2017 | MacMullan | H04L 43/0829 |
| 2018/0007704 A1 | 1/2018 | Deierl | |
| 2018/0160450 A1 | 6/2018 | Bashar | |
| 2020/0330011 A1* | 10/2020 | Honore | A61B 5/1455 |
| 2021/0136618 A1* | 5/2021 | Liu | H04W 36/30 |
| 2021/0204287 A1* | 7/2021 | Tsai | H04W 72/02 |

FOREIGN PATENT DOCUMENTS

| | | |
|---|---|---|
| EP | 2207395 A2 | 7/2010 |
| WO | 2007034650 A1 | 3/2007 |
| WO | 2015034993 A1 | 3/2015 |
| WO | 2018127765 A1 | 7/2018 |

OTHER PUBLICATIONS

Islam, Z. et al., "Efficient Techniques for Improving Coexistence Problem in Wireless Body Area Network", 19th International Conference on Computer and Information Technology, Dec. 2016.

* cited by examiner

RECOMMENDING WHETHER A SUBJECT MONITORING SYSTEM USES A WIRELESS COMMUNICATION MODE

This application is the U.S. National Phase application under 35 U.S.C. § 371 of International Application No. PCT/EP2020/055610, filed on 4 Mar. 2020, which claims the benefit of European Application Serial No. 19162555.7, filed 13 Mar. 2019. These applications are hereby incorporated by reference herein.

FIELD OF THE INVENTION

The present invention relates to the field of subject monitoring systems, and in particular to methods of communicating between sensors and a communications module of a subject monitoring system.

BACKGROUND OF THE INVENTION

Subject monitoring systems are becoming of increasing interest in the medical field. Such systems typically comprise one or more sensors for measuring a medically relevant parameter, which are usually small, autonomous devices that can be individually placed at appropriate locations on the body of a subject/patient. The sensors can pass measured parameters to a communications module, which may be partially or completely integrated into a patient monitor. The patient monitor can be responsible for displaying, alarming and documenting parameters measured by the sensors.

There is a desire to operate sensors in the subject monitoring system wirelessly, thereby setting up a medical body area network (MBAN), as this improves patient comfort. In particular, wireless sensors allow the subject freedom of movement, and means that staff do not need to be concerned with wires getting in the way during examination (which is a significant source for accidents). Freedom of movement is particularly important in the area of obstetrics, as this allows a monitored mother to freely move (e.g. walk around or change position) thereby reducing pain of birth progress.

However, wireless connections are much more susceptible to interference than wired connections. Indeed, as wireless technology continues to be implemented into everyday devices (i.e. the advent of the Internet-of-Things) the potential for interference in a wireless connection is significantly increased, especially in a clinical setting. A particular complicating factor is that interferers may appear intermittently or at short notice.

It is particularly desirable that communications between the sensor(s) and the communications module for the subject monitoring system use a reliable and undisturbed communication link, as data packets cannot be resent if they are not received, unlike in a typical wireless local area network (WLAN). In a clinical setting, sudden and unexpected data dropouts can have hazardous, and potentially life-threatening, consequences, e.g. as changes in a patient condition may go unnoticed. There is therefore a conflict between the desire for a reliable communication link, and the desire for improved patient comfort.

SUMMARY OF THE INVENTION

The invention is defined by the claims.

According to examples in accordance with an aspect of the invention, there is provided a method of recommending whether or not a subject monitoring system should use a wireless communication mode to communicate data between at least one sensor and a communications module of the subject monitoring system. The method comprises: determining, at the communications module, a first noise value for each of a plurality of channels in which the at least one sensor and the communications module, when the subject monitoring system operates in a wireless communication mode, are able to communicate; determining the number of eligible channels for wireless communication having the first noise value below a first predetermined threshold; and recommending whether or not a wireless communication mode should be used based on the determined number of eligible channels.

The present invention recognizes that a decision can be made as to whether to use wireless communications between a sensor and a communications module of a subject monitoring system. However, users of such a system (e.g. caregivers or clinicians) are typically unaware of possible impairments of wireless transmission prior to activation of wireless sensors. The herein described concept enables an automated recommendation of whether a wireless communication mode is appropriate based on a number of wireless channels with a noise below a certain level, i.e. predicted to allow reliable wireless communication. Thus, a wireless communication mode can be recommended only when it is ensured (with a certain degree of probability) that communications between a sensor and a communications module will be reliable. This ensures that a more comfortable wireless communication mode is recommended when the wireless communication mode is sufficiently reliable.

In other words, the method determines whether a wireless communication mode will be sufficiently reliable for communications between sensors and a communications module based on a number of wireless channels that are determined to be eligible for reliable wireless communication (having a noise value below a certain threshold). If the wireless communication mode is deemed sufficiently reliable, it is recommended (to improve patient comfort), otherwise, it is not recommended.

By way of example, a step of recommending that a wireless communication mode is not used may comprise recommending that a wired communication mode is used (instead). This is because reliable communications take precedence over patient comfort due to the possible consequences of data dropout(s). In some embodiments, a step of recommending that a wireless communication mode is not used may comprise recommending that a hybrid communication mode is used, in which communications between a communications module and a group of sensors use both wired and wireless communication methodologies. In some embodiments, the step of recommending that a wireless communication mode is not used may comprise recommending that the user use an alternative subject monitoring system (e.g. a wired subject monitoring system) to monitor parameters of the subject.

Thus, a user-friendly recommendation of whether a wireless communication mode is appropriate can be provided without the need for specialist equipment or technically knowledgeable operators. In particular, a recommendation can be made in advance of using the subject monitoring system, therefore reducing the likelihood of communication dropouts during use of the subject monitoring system.

A wireless communication mode may be a mode in which communications between the sensor(s) and the communications module only take place wirelessly. Other communication modes may include a wired communication mode (in which communications between sensor(s) and communications module take place over wires), a hybrid communication (in which some sensors communicate using wires and others communicate wirelessly) and a non-communicative/standby mode (in which the communications module and sensors do not attempt to communicate).

Preferably, the first noise value comprises a received signal strength indicator, RSSI, value. An RSSI value is here used to indicate whether a channel is occupied or in use by another system, e.g. a(nother) medical body area network in the immediate vicinity. By assessing whether a channel is in use, an effective prediction as to possible interference on that channels can be made. Thus, using an RSSI value as a noise measurement of a channel enables an assessment of the use of available or possible wireless communications to be made accurately, whilst taking into account possible interferers. In particular, the presence of potential interferers of a wireless communication can be identified.

Examples of suitable RSSI values include: a maximum RSSI value (within a certain time period), minimum RSSI value (within a certain time period), range of RSSI values (within a certain time period) or average RSSI value (within a certain time period).

Preferably, the first noise value comprises an average RSSI value obtained over a period of at least 30 minutes. Interferers in a channel may be intermittent or periodic. It is therefore preferable to assess the RSSI value over a long period of time. This reduces the likelihood that the presence of an intermittent interferer is missed, when compared to using only an instant value of the RSSI, and a wireless communication mode recommended even though it may actually be unreliable.

Preferably the average RSSI value is obtained over a period of at least an hour, even more preferably at least six hours, even more preferably at least a day. A longer period for obtaining the RSSI value (e.g. >30 minutes) enables interferers that communicate only periodically (as is common in a clinical setting) to be identified, thereby increasing a reliability of determining whether a wireless communication mode is sufficiently reliable.

The step of recommending whether or not a wireless communication mode should be used may comprise: recommending that a wireless communication mode is not used if the number of eligible channels is below a first predetermined number; and recommending that a wireless communication mode is used if the number of eligible channels is above or equal to the first predetermined number.

Thus, the number of available or eligible channels defines whether or not a wireless communication mode is recommended. When the number of eligible channels is low, it is determined that a wireless communication mode would be unreliable and therefore is not recommended. When the number of eligible channels is high, it is determined that a wireless communication mode is sufficiently reliable and is therefore recommended.

In some examples, the first predetermined number may be 1. Thus, embodiments may effectively predict whether there are any available channels for wireless communication in which to reliably communicate. However, the first predetermined number may be different in other embodiments. For example, the first predetermined number may be 2 or 5 or 10. Preferably, the first predetermined number is no greater than 5, and/or no less than 1. The first predetermined number may depend, for example, on the number of channels required to communicate between the sensors and the communications module. In other examples, the number of channels may be greater than 1 to enable a communication between the sensor(s) and the communications module to switch channel in the event of an unexpected or previously undetected interferer (e.g. using a smart hopping technique). Other reasons for selecting a higher predetermined number will be apparent to the skilled person. The higher the first predetermined number, the greater the probability that the wireless communication mode will, in practice, be reliable.

In some examples, the first predetermined number is a fraction or percentage of the number of the plurality of channels, e.g. no less than 20% or 40% of the plurality of channels. The number of the plurality of channels may depend upon the wireless communication protocol used. For example, ZigBee® offers to break a band into 16 separate channels, whereas Bluetooth® can offer around 79 different channels. The first predetermined number may be a minimum number for ensuring (with a certain probability) reliable and continuous wireless communications, e.g. 20% or 40% of the total number of channels.

The step of recommending whether or not a wireless communication mode should be used may comprise, in response to the number of eligible channels being above a second predetermined number: determining whether or not there are at least three adjacent eligible channels; in response to determining that there are at least three adjacent eligible channels, recommending that a wireless communication mode is used; and in response to determining that there are not at least three adjacent eligible channels, either: recommending that a wireless communication mode can be used, but may be unreliable; or recommending that a wireless communication mode is not used.

For a better resolution and greater certainty in the prediction about the reliability of wireless communication, the method may determine whether there are at least three adjacent eligible channels. Communications from possible wireless interferers within a particular channel may bleed into other channels (e.g. if they are operating according to a different communication protocol to the MBAN which could be formed by the subject monitoring system). By ensuring that there are at least three adjacent eligible channels, a probability that at least one of these channels (i.e. the center channel(s)) will have sufficiently low interference for reliable communication is increased.

In other words, it cannot be guaranteed that an eligible channel will not be subject to interference due to possible bleeding from adjacent channels. However by ensuring that there are at least three adjacent channels, before recommending a wireless communication mode, a probability that at least one of the identified eligible channels will not be subject to wireless interference is increased.

The second predetermined number is preferably greater than the first predetermined number, although this is not essential. For improved efficiency of performing the method, the second predetermined number may be no less than 2 (as the subsequent steps comprise determining whether there are three adjacent channels).

The step of recommending whether or not a wireless communication mode is used preferably comprises, in response to the number of eligible channels being at or below the second predetermined number: recommending that a wireless communication mode is not used if the number of eligible channels is below a first predetermined number; recommending that a wireless communication mode can be used, but may be unreliable, if the number of eligible channels is above or equal to the first predetermined number.

Thus, if there are not at least three adjacent channels, the probability that a channel will be available for reliable wireless communication is reduced. Thus, it cannot be guaranteed (with a certain degree of probability) or predicted that a wireless communication mode will be reliable.

The step of, in response to determining that there are at least three adjacent eligible channels, recommending that a wireless communication mode is used may comprise: recommending that a wireless communication mode be used in which a wireless communication takes place over an eligible channel, disposed directly between two other eligible channels.

Thus, a sub-mode in which a certain channel is used for wireless communication is recommended when three adjacent channels are present. This increases the probability that a wireless communication will be reliable, as the channel most likely to be reliable is recommended for use.

The method preferably comprises determining, at the communications module, a time occupied value for each of the plurality of channels, the time occupied value being a length of time for which a second noise value of each of the channels is above a second predetermined threshold, wherein the step of determining the number of eligible channels for wireless communication comprises determining the number of eligible channels having the first noise value below the first predetermined threshold and the time occupied value below a third predetermined threshold.

Thus, the length of time for which a noise value is above a certain threshold is used to identify whether a particular channel is eligible for wireless communication or not (i.e. is not too noisy). The first noise value may be an average received signal strength indicator, RSSI, value and the second noise value may be a (instant) received signal strength indicator, RSSI, value.

In embodiments, the step of determining, at the communications module, is performed only when the communications module is not in wireless communication with the at least one sensor. Thus, the recommendation may be performed before the subject monitoring system sets up an MBAN or is monitoring patient/subject parameters.

In other embodiments, the step of determining may be performed when the communication module is in wireless communication with the at least one sensor, for example, by using a time multiplexed system or by using a separate, dedicated wireless transceiver.

In at least one embodiment, the step of recommending a communication mode may comprise generating a user perceptible output of the recommended communication mode, such as an audio, visual (e.g. text or a traffic-light output) or haptic output (e.g. a vibration). Such an output would assist a user in performing a technical task of selecting or controlling a communication mode of an subject monitoring system to ensure suitable communication reliability, whilst taking into account the desire to use wireless communication modes, e.g. for subject comfort.

There is also proposed a method of selecting (or entering) a communication mode to be used by a subject monitoring system for communicating between at least one sensor and a communications module. The method comprises: recommending whether or not a wireless communication mode should be used by performing any previously described method; and selecting (or entering) the wireless communication mode if it is recommended (i.e. in response to it being recommended) to use the wireless communication mode. Preferably, the wireless communication mode is not selected or entered if it is recommended to not use the wireless communication mode, i.e. an alternative communication mode is entered instead, such as a wired/hybrid/standby mode.

Thus, the recommended communication mode may be automatically set in the subject monitoring system. Thus, the receiver and/or sensors may be automatically set to operate in a wireless mode, thereby determining whether wireless (e.g. MBAN) network is set up. This reduces a likelihood of user error from selecting an inappropriate communication mode.

In some embodiments, the step of recommending that a wireless communication mode is not used may comprise disabling a wireless transceiver (e.g. of the communications module), to thereby prevent the subject monitoring system from operating in the wireless communication mode. This may be performed using appropriate software.

According to examples in accordance with an aspect of the invention, there is also provided a computer program comprising code means for implementing the method any described method when said program is run on a processing system, such as a computer.

According to examples in accordance with an aspect of the invention, there is provided a communications module for a subject monitoring system, the communications module being operable to communicate with at least one sensor when the subject monitoring system operates in a wireless communication mode.

The communications module comprises a processing system adapted to: determine a first noise value for each of a plurality of channels in which the at least one sensor and the communications module, when operating in a wireless communication mode, are able to communicate; determine the number of wireless communication channels having the first noise value below a predetermined threshold; and recommend whether or not a wireless communication mode is used by the subject monitoring system based on the determined number of wireless communication channels.

The processing system may be adapted to determine the first noise value of each of the plurality of channels only when the communications module is not in wireless communication with the at least one sensor.

There is also proposed a subject monitoring system comprising: the communications module previously described; and one or more sensors, for monitoring a subject, able to wirelessly communicate with the communications module when the subject monitoring system operates in a wireless communication mode.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

According to a concept of the invention, there is proposed a way to recommend in what manner or mode a sensor and communications module of a subject monitoring system should communicate. A determination is made as to whether or not more than a predetermined number of wireless channels have a noise level below a certain threshold. If a positive determination is made, a wireless communication mode is recommended. If a negative determination is made, a wireless communication mode is not recommended.

Embodiments are at least partly based on the realization that it is preferably to monitor a subject using wireless sensors for comfort, but that such wireless sensors may not be entirely reliable. It is also realized that a user of a subject monitoring system is typically not able to understand or interpret when wireless communications will be reliable. It is therefore proposed, if a wireless connection can be reliably made and maintained, then a wireless communication mode is recommended, otherwise it is not recommended (e.g. a wired communication mode may instead be recommended). Embodiments take into account the need or desire for communications between sensors and a communications module to be continually reliable, whilst acknowledging the desire for improved patient comfort.

Illustrative embodiments may, for example, be employed in a clinical setting, such as obstetrics, to minimize discomfort to a (pregnant) subject whilst ensuring communications are reliable.

A "channel" or "wireless channel" is a predetermined range of frequencies, typically centered about a center frequency which can be used to identify the channel. Typically, the range of frequencies covered by a particular channel is defined by a wireless communication protocol, e.g. the IEEE 802.11 protocol, which may be able to define a center frequency and width of the channel.

Figure 1:
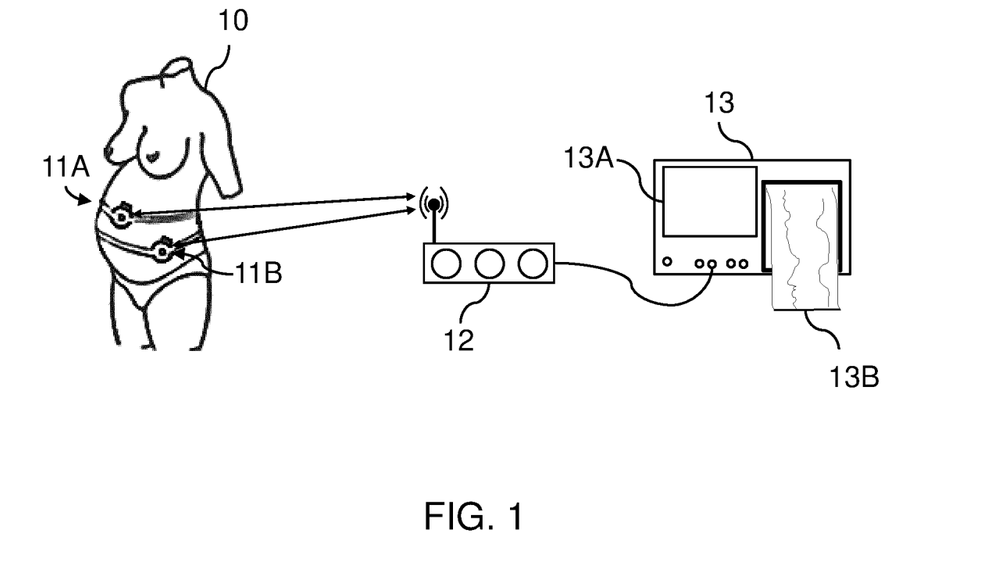
FIG. 1 illustrates a subject monitoring system for understanding a context of embodiments of the invention.

FIG. 1 illustrates a subject monitoring system for understanding a context in which embodiments may be employed. The subject monitoring system is here adapted for use in obstetrics, although other uses are envisaged.

The subject monitoring system is adapted to monitor one or more parameters of subject 10. One or more sensors 11A, 11B capture one or more parameters of the subject, such as fetal heart rate, uterine activity, maternal pulse and so on. The one or more sensors 11A, 11B may be connected to the subject using one or more elastic belts (as illustrated), or using an appropriate adhesive, such as a weak or gummy adhesive. Each sensor may, for example, capture a different parameter of the subject, or more than one sensors may work collectively to monitor a specific parameter or parameters (e.g. two separate sensors can monitor fetal heart rate to improve an accuracy and reliability of the monitored parameter).

Each sensor 11A, 11B passes a respective monitoring signal, carrying monitored parameters, to a communications module 12, which is in turn directly connected to a patient monitor 13. The patient monitor 13 records the monitoring signal(s) on a memory. The patient monitor may provide a visual display 13A of a current parameter of the patient (e.g. display a current fetal heart rate) and/or provide a printout 13B of the parameters monitored by the sensors to enable a clinician to understand the long-term progress of the subject.

In some embodiments, the communications module 12 is integrated into the patient monitor 13, so as to form part of the patient monitor 13. In other embodiments, as illustrated, the communications module 12 is separate from the patient monitor 13 but able to communicate therewith, e.g. via one or more wires. The communications module 12 may be split, so as to be partly integrated into the patient monitor and partly formed as a separate component.

At least some of the one or more sensors 11A, 11B and the communications module 12 of the illustrated subject monitoring system are able to communicate using at least a wireless communication methodology. For example, at least some of the one or more sensors may be able to communicate using only a wireless communication methodology (and may not be able to communicate using a wire).

In embodiments, the subject monitoring system comprises at least some (others) of the one or more sensors 11A, 11B are only able to communicate via a wire.

In some embodiments, at least some of the one or more sensors are able to communicate with the communications module using both a wireless communications methodology and a wired communication methodology (although, preferably, only one is selected at any given time). Thus, some sensors may be switchable between a wireless and a wired communication mode (e.g. be able to communicate either wirelessly or using wires), effectively being hybrid sensors.

Thus, any given sensor may be able to communicate in a wireless and/or wired communication mode.

Not all of the sensors for a subject monitoring system need to be "active" (i.e. in communication with the communications module) at a given time to enable monitoring of the subject. For example, a subject monitoring system may comprise a first group of one or more wireless sensors and a second group of one or more wired sensors, where only one of the first and second group are active and used to monitor the subject at a given time (e.g. depending upon an active communication mode). Of course, a combination of wired and wireless sensors may be used to monitor the subject.

Other subject monitoring systems, in which the invention is not employed, may comprise only sensors able to communicate using wires. The present invention relates to subject monitoring systems that comprise at least some sensors able to communicate with the communications module wirelessly.

Thus, the subject monitoring system can be operated in at least a wireless communication mode, in which sensor(s) 11A, 11B and communications module 12 communicate using a wireless communication protocol, effectively setting up a medical body area network (MBAN). Preferably, in the wireless communication mode, only sensors having wireless communication capability are able to communicate with the communications module.

The subject monitoring system may also be operable in a non-communicative mode, in which it is unable or prohibited from attempting to communicate with sensors. This non-communicative mode may be labelled a "stand-by" mode.

In some embodiments, the subject monitoring system may be further operable in a wired communication mode, in which sensor(s) 11A, 11B and communications module 12 communicate via one or more wires. Preferably, in the wired communication mode, only sensors able to communicate via a wired are able to communicate with the communications module (e.g. a wireless capability of the communications module is deactivated).

In some embodiments, the subject monitoring system may be operable in a hybrid communication mode, in which one or more sensors communicate using a wireless communication protocol and at least one other sensor communicates via one or more wires, where both sets of sensors are active.

Suitable wireless communication protocols that may be used include ZigBee®, Bluetooth®, a wireless local area network protocol such as in accordance with the IEEE 802.11 standards, a 2G, 3G or 4G telecommunication protocol, and so on. Other formats will be readily apparent to the person skilled in the art. The wireless communication protocol defines how many different channels devices could use in an attempt to communicate wirelessly.

In some embodiments, when at least some wireless sensors are active, each wireless sensor communicates with the communications module using a different channel. In other embodiments, when at least some wireless sensors are active, a channel can be shared between more than one wireless sensor (e.g. all sensors may share a same channel, e.g. if time-division multiplexing is used).

The communications module and sensors may employ, when at least some wireless sensors are active, a channel hopping technique. Such techniques are known to the skilled person.

Figure 2:
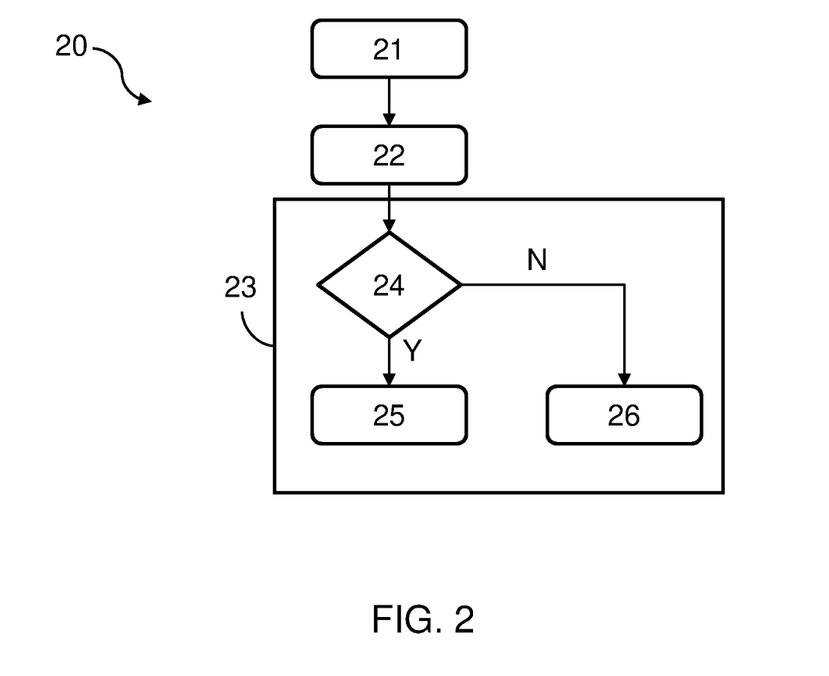
FIG. 2 is a flowchart illustrating a method according to an embodiment of the invention.

FIG. 2 illustrates a method 20 for recommending a communication protocol according to a first embodiment of the invention.

The method 20 comprises a step 21 of determining a first noise value for each of a plurality of channels. Each of the channels is a range of frequencies in which the sensor and communications module can communicate.

As previously explained, the size and frequency range of a channel may depend upon the particular wireless protocol(s) that the sensors and communications module can use to communicate. Preferably, the plurality of channels itself forms a continuous range of frequencies, i.e. the channels abut one another. The number, size and configuration of the plurality of channels depends upon the particular wireless protocol(s) that the sensors and communications module are able to communicate, as would be appreciated by the skilled person. In particular, it is recognized that the width and range of each channel varies for different wireless protocols.

The first noise value obtained in step 21 is a measure of channel occupancy or noise. Preferably, the first noise value is a measure or parameter of radio signal information, such as radio signal strength indicator (RSSI), which indicates whether the channel is occupied by another communicative device (such as a(nother) MBAN). Other embodiments may use any measure of noise, such as a power level (e.g. in dBm) of signals in a channel.

Preferably, the first noise value is an average RSSI, preferably, obtained over a period of at least 30 minutes, such as at least an hour. In some embodiments, the average RSSI is further processed to determine a relative proportion or percentage to a maximum known or possible RSSI value (e.g. a historic maximum RSSI value). Thus, the first noise value may be an average percentage of the RSSI relative to a maximum known RSSI level (as obtained over a certain period of time, e.g. no less than 30 minutes).

In other words, step 21 comprises obtaining data about each particular channel, where the data indicates a certain noise level or other value representing an occupancy level of each channel.

The method 20 further comprises a step 22 of determining a number of eligible channels for wireless communication, having the first noise value below a first predetermined threshold.

The first predetermined threshold may represent a noise level above which signals between a sensor and communications module of a subject monitoring system, within that channel, are deemed unreliable (e.g. may become undistinguishable from noise or other interference). Thus, step 22 effectively comprises counting the number of channels having a sufficiently low noise level to enable reliable wireless communication. In particular, the first predetermined threshold may define whether a channel is, on average, unoccupied by another source and therefore free to communicate over with a high degree of reliability. Where the first noise value is an average RSSI, the first predetermined threshold may be no more than −75 dBm, e.g. no more than −85 dBm.

The method 20 further comprises a step 23 of recommending whether or not a wireless communication mode should be used based on the determined number of eligible channels. In this way, step 23 recommends whether or not a wireless communication mode should be used based on the number of channels that allow for reliable wireless communication.

In the illustrated example, step 23 comprises a sub-step 24 of determining whether the number of eligible channels is (or is not) more than or equal to a first predetermined number.

In response to sub-step 24 determining that there are more than or equal to a first predetermined number of eligible channels, a sub-step 25 is performed. In response to sub-step 24 determining that there are less than a first predetermined number of eligible channels, a sub-step 26 is performed. Sub-step 25 comprises recommending that a wireless communication mode is used. Sub-step 26 comprises recommending that a wireless communication mode is not used, e.g. by recommending that a wired communication mode is used.

Thus, step 23 comprises recommending whether or not a wireless communication mode is used based on a comparison between the number of eligible channels and a predetermined number. In this way, a wireless communication mode is only recommended if a suitable number of eligible channels are available to ensure a reliable wireless connection between the at least one sensor and the communications module.

The first predetermined number may, for example, be 1. Thus, step 24 may comprise determining whether or not there are any eligible channels. In response to step 24 determining that there is at least one eligible channels, sub-step 25 of recommending that a wireless communication mode is used is performed. In response to step 24 determining that there is not at least one eligible channel, sub-step 26 of recommending that a wireless communication mode is not used (e.g. that a wired communication mode is used instead, if available) is performed. Setting the first predetermined number to a value of 1 simplifies the method, as step 24 would merely need to determine whether there are any eligible channels.

However, the first predetermined number may be greater than 1 in other embodiments. For example, some embodiments may wish for the communications module to communicate using more than one channel. In one example, the first predetermined number is equal to the number of sensors to be used, so that each sensor is able to communicate using a separate channel. This would reduce inter-sensor interference. In another example, there may be a regulatory requirement specifying a certain duty cycle for a given channel for wireless communications, in this case more than one channel (e.g. two or three channels) may be necessary to enable a sensor or communications module to switch between the more than one channels to adhere to the regulatory requirement(s) whilst maintaining continuous wireless communications.

A first predetermined number greater than 1 will also increase the probability that the prediction that the wireless communication mode will be reliable is correct in practice. This is because there would be a greater number of channels for the communications module or sensor(s) to use or exploit, e.g. in the event that a channel used by the communications module or sensor(s) becomes noisy during wireless transmission due to an undetected or new interferer.

Figure 3:
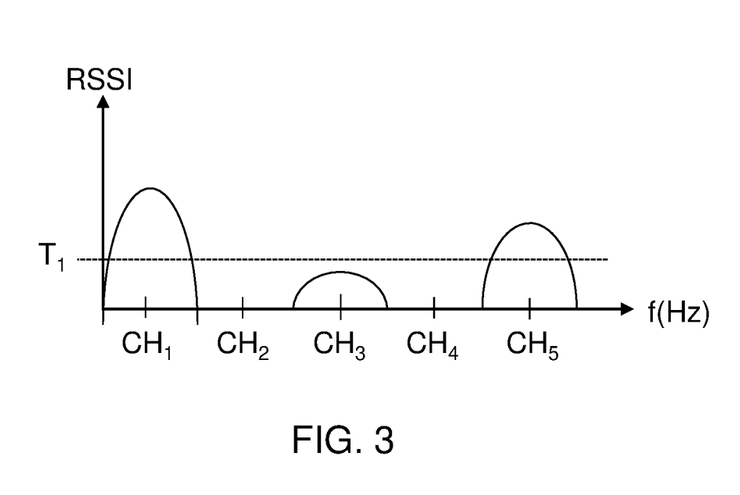
FIG. 3 is a graph illustrating a plurality of channels.

The step 23 of recommending whether or not a wireless communication mode is used may comprise presenting a clinician-perceptible output (i.e. a user notification) of the recommended mode. This output may, for instance, be a message provided on a display (such as the display 13A of the patient monitor 13), an optical indicator such a traffic light signal (e.g. green means wireless communication mode recommended, red means wireless communication mode is not recommended), an acoustic signal and so on. The step of presenting a clinician-perceptible output may be integrated into the sub-steps 25, 26. Further examples of presenting a clinician-perceptible output are provided later. For the sake of further explanation, FIG. 3 is an exemplary graph illustrating a measured RSSI for a plurality of different channels $CH_1$-$CH_5$. A first predetermined threshold $T_1$ is illustrated. A first $CH_1$ and fifth $CH_5$ channel have an RSSI above the first predetermined threshold $T_1$. The second $CH_2$, third $CH_3$ and fourth $CH_4$ channel have an RSSI below the first predetermined threshold $T_1$, and are therefore termed "eligible channels".

Figure 4:
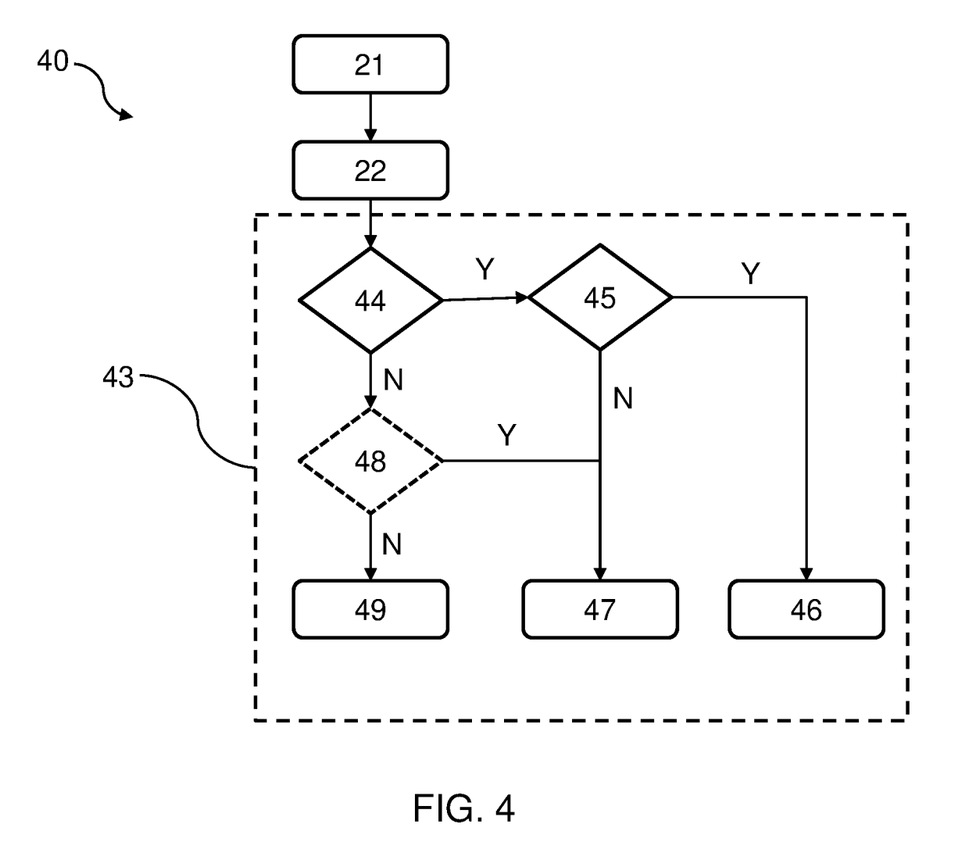
FIG. 4 is a flowchart illustrating a method according to another embodiment of the invention.

FIG. 4 illustrates a method 40 for recommending whether or not a wireless communication mode is used according to a second embodiment of the invention.

The method 40 differs from the method 20 of the first embodiment by way of a different step 43 of recommending whether or not a wireless communication mode is used. Thus, method 40 also comprises a step 21 of determining a first noise value for each of a plurality of channels and a step 22 of determining a number of eligible channels for wireless communication, having the first noise value below a first predetermined threshold.

Step 43 of method 40 comprises a sub-step 44 of determining whether (or not) the number of eligible channels is greater than or equal a second predetermined number. The second predetermined number may be different to the first predetermined number, and is preferably at least three.

In response to a positive determination in sub-step 44 (i.e. there are at least the second predetermined number of channels), a sub-step 45 is performed. Sub-step 45 comprises determining whether (or not) there are at least three adjacent eligible channels. Thus, sub-step 45 comprises determining whether there is a sequence of at least three channels that sequentially abut one another. This effectively determines whether there is at least one eligible channel that is directly disposed (i.e. without intervening channels) between two other eligible channels.

In response to a positive determination in sub-step 45 (i.e. when there are at least three adjacent channels), the method comprises a sub-step 46 of recommending that a wireless communication mode is used.

In response to a negative determination in sub-step 45, the method can comprise either performing a sub-step 49 (the link between sub-step 45 and sub-step 49 not being illustrated) of recommending that a wireless communication mode is not used or a sub-step 47 (as illustrated) of recommending that a wireless communication mode can be used, but that it may be unreliable or "questionable". Sub-step 47 may also comprise recommending that a wired communication mode can be used if available (e.g. as an alternative to the wireless communication mode). Sub-step 49 may comprise recommending that a wired communication mode is used, if available.

Thus, a wireless communication mode is only recommended for use if there is an eligible channel (or eligible channels) that is disposed directly between two other eligible channels. This increases a probability that a wireless communication mode will be reliable, as an eligible channel can be chosen that has a reduced likelihood of signals in illegible adjacent channels "bleeding" into the chosen channel(s) (e.g. due to changes in power of signals in such channels or the use of different wireless communication protocols).

In response to a negative determination in sub-step 44, the method may perform a sub-step 48 of determining whether (or not) there are at least a first predetermined number of eligible channels. In response to a positive determination in sub-step 48 (i.e. there are at least the first predetermined number), then either sub-step 46 (the link between sub-step 48 and sub-step 46 not being illustrated) or (preferably, and as illustrated) sub-step 47 is performed. Sub-step 46 may be performed if the first predetermined number represents a suitable number for ensuring that there is a reliable wireless communication. Sub-step 47 may be performed as a default state, e.g. when the first predetermined number is 1.

In response to a negative determination in sub-step 48 (i.e. there are less than the first predetermined number of eligible channels), then the method performs a sub-step 49 of recommending that a wireless communication mode is not used.

Alternatively, in response to a negative determination in sub-step 44, the method may directly perform sub-step 49 of recommending that a wireless communication mode is not used. Thus, sub-step 48 is optional.

Further embodiments of the invention may also comprise, if the methods performs a step of recommending a wireless communication mode is used, recommending a particular channel or channels to use. For example, a step of recommending a wireless communication mode may comprise recommending that an eligible channel, that is disposed directly between two other eligible channels, is used to perform wireless communication between a sensor and the communications module (e.g. in method 40). As another example, a step of recommending a wireless communication mode is used may comprise recommending that the eligible channel (or channels) having the lowest first noise value is used to perform wireless communication between a sensor and the communications module.

More than one channel may be recommended for use, for example, for communicating with different sensors. Alternatively, more than one channel may be recommended to provide an option for a clinician.

The above-described methods are particularly advantageous when used in a static environment. However, it is recognized that wireless signals in an environment may be more complex, for example, due to short-term or periodically recurring radio activities with varying signal strength. In particular, in a clinical setting such as a hospital, there may be a large number of different wireless systems in use, which may not have identical radio characteristics, e.g. different bandwidth occupations, duty cycles, signal strengths etc., as well as different distances from the subject monitoring system in question. It can be assumed that the usage of these systems will be randomly distributed, meaning that they will occupy channels for different periods of time. The dynamic bandwidth occupancy means that at first point in time, only a first set of channels will be eligible available and a second, different point in time only a second, different set of channels (e.g. fewer) will be eligible.

Thus, to improve the reliability of predicting the reliability of a wireless channel (or the plurality of the channels), a long-term observation of the channels could be used. Thus, each channel may be monitored for a period of no less than half an hour, e.g. no less than an hour, e.g. no less than 3 hours. Monitoring a channel may be performed continually or by periodically sampling or assessing a noise value of the channel(s).

In a particular embodiment, the method may further comprise determining a time occupied value for each of the plurality of channels, the time occupied value being a length of time for which a second noise value of each of the channels is above a second predetermined threshold. In particular, the time occupied value may be calculated over a certain period of time (e.g. over the course of 30 minutes or over the course of an hour).

The time occupied value may, for example, be a percentage of time that the second noise value is above a second predetermined threshold within a predetermined period of time (i.e. over a period of time that the communications module monitors the channel).

Figure 5:
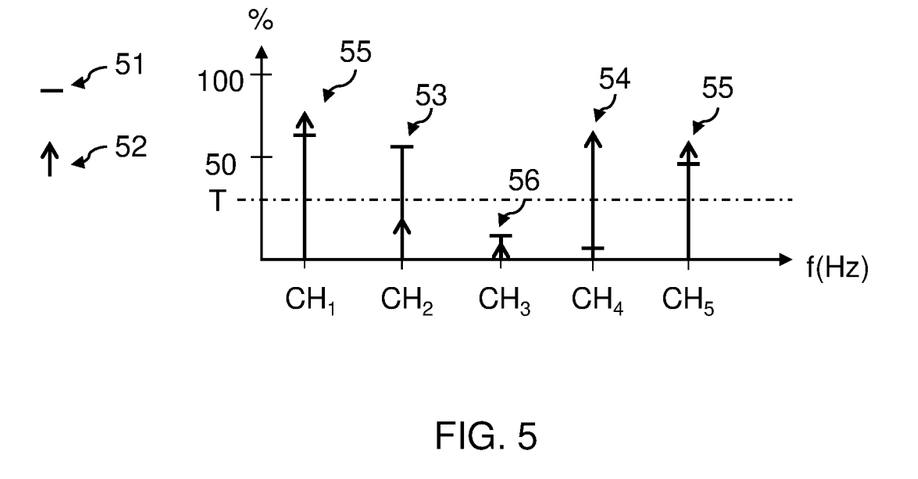
FIG. 5 is a graph illustrating different noise values for a plurality of channels.

FIG. 5 illustrates an embodiment in which both a first noise value 51 and a time occupied value 52 are obtained for each channel $CH_1$-$CH_5$. Here, the first noise value represents the average percentage of the RSSI relative to a maximum known RSSI level. The time occupied value is a percentage of the monitored time for which a second noise value (e.g. a magnitude of the RSSI) is above the second predetermined threshold.

A dash symbol 51 represents the first noise value and an arrow 52 represents the time occupied value. Using the first noise value 51 and the time occupied value 52 enables a long term evaluation of the channel reliability.

When both values 51, 52 are above a respective predetermined threshold T (which, as illustrated, may be the same for each value 51, 52), then that channel 55, $CH_1$, $CH_5$ is completely unusable (i.e. it is too noisy to allow for reliable communications).

A low time occupied value (e.g. below a threshold T) and a high average RSSI value (e.g. above the threshold T) is an indicator of an intermittent interferer in the channel 53, $CH_2$, so that the frequency may be considered unreliable over a period of time.

A high time occupied value 52 and a low average RSSI value 51 is an indicator that there is probably a permanent, but distant, interferer in the channel 54, $CH_4$. Although such channels may be eligible for use in reliable communication (due to the low noise level), they are less preferred than when both observation values are low, as characteristics of the permanent interferer are more likely to change over time (e.g. due to patient movement to a different area of the clinical setting).

When both observation values are low, e.g. below the threshold T, as in channel 56, $CH_3$ this is indicative of an eligible channel that is suited for a reliable and trouble free operation of a wireless network, as this channel appears to be unused in the immediate and distant vicinity.

Thus, in some preferred embodiments, the step of determining the number of eligible channels for wireless communication may comprise determining the number of channels having a first noise value below a first predetermined threshold and a time occupied value below a third predetermined threshold (the second predetermined threshold being used in the calculation of the time occupied value).

The first and third predetermined thresholds may be the same, in particular where both the first noise value and the time occupied value are percentages, fractions or are otherwise on a same/similar scale.

Such an embodiment increases a likelihood that the channels identified as being eligible will remain noise-free during the operation of a potential wireless communication between the sensor(s) and the communications module of the subject monitoring system.

It has previously been described how embodiments of the invention may also comprise, if recommending a wireless communication mode is used, recommending a particular channel or channels to use. In one embodiment, the step of recommending a wireless communication mode may comprise recommending that a channel having the lowest first noise value 51 and/or lowest time occupied value 52 is used. In other examples, the step of recommending that a wireless communication mode may comprise recommending that a channel having the lowest sum (e.g. if they are on a same scale) or weighted sum (e.g. if they are not on the same scale) of at least the first noise value 51 and the lowest time occupied value 52 is used.

It should be understood that use of an average RSSI value for the first noise value (used in any described embodiment) is only one example of a possible first noise value. Many other suitable first noise values are imaginable, e.g. minimum RSSI, maximum RSSI and/or mean RSSI. The obtained data for characterizing the channel, e.g. the first noise value and the lowest time occupied value or historic monitored values used in the calculation of such values, should be ideally stored in a non-volatile memory to have this data available after a power interruption.

It can be assumed that the communications module typically is not mobile so that the radio related conditions are reasonably constant over time. The combination of the snapshot values and the historical data (e.g. time occupied value) give a precise reliability prediction of the radio link.

The step of recommending whether or not a wireless communication mode is used may comprise generating a user-perceptible output (e.g. an audio, visual or haptic output). The user perceptible output may indicate whether a wireless communication mode is recommended.

In some embodiments, the presence of a user perceptible output (e.g. an alarm) indicates that a wireless communication mode is not recommended (e.g. that a wired communication mode is recommended instead) and the absence of a user perceptible output (e.g. no alarm) indicates that a wireless communication mode is recommended. Thus, under normal operation conditions the reliability prediction may not be required, but in case of abnormal, unforeseeable conditions the user will receive a warning prior to the activation of the wireless network. In this way, in the event of case of a warning the user has sufficient time to activate an alternative connection method e.g. use of sensors with cables.

Preferably, the step of determining a first noise value (and optionally the second noise value) for each of the plurality of channels is only performed when the communications module is not in wireless communication with any sensors. This improves a reliability of wireless communication between the sensors and the communications module, as any wireless transceivers are not dividing their time between communicating patient parameters and monitoring data of channels.

Of course, in some embodiments, determining the first noise value for each of the plurality of channels may be performed when the communications module is in wireless communication with the sensors, e.g. if the communications module comprises a dedicated receiver for monitoring the channels.

In other examples, a single receiver is adapted to monitor the channels and perform communications, e.g. by using a time-division system to alternate between communications and monitoring of the channels.

Figure 6:
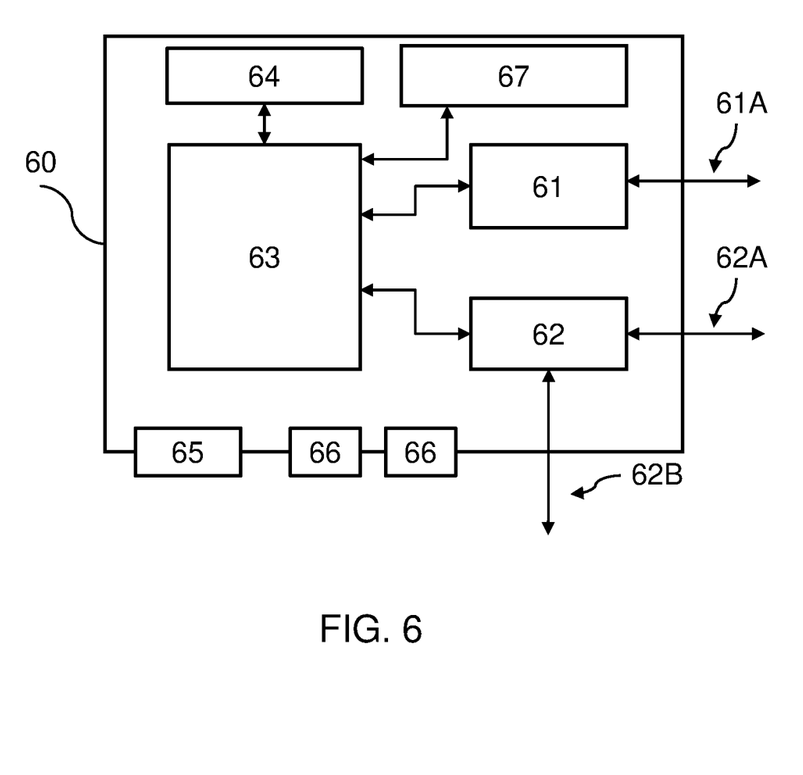
FIG. 6 illustrates a communications module for a subject monitoring system according to an embodiment of the invention.

FIG. 6 illustrates a communications module 60 for a subject monitoring system according to an embodiment of the invention. The communications module 60 is designed to communicate with at least one sensor (not shown).

The communications module 60 comprises a wireless transceiver 61 (or radio unit or base station) for sending and/or receiving wireless signals 61A to/from at least one sensor.

The communications module is operable in at least a wireless communication mode, in which communication with the at least one sensor take place over the wireless transceiver 61. The subject monitoring system may also be operable in a non-communicative mode, in which it is unable or prohibited from attempting to wirelessly communicate with sensors.

The communications module 60 may also comprise a wired modem 62 for sending and/or receiving wired signals 62A to/from at least one sensor. The wired modem is an optional feature of the communication module. In such embodiments, the communication module may be operable in a wired communication mode, in which communication with at least one sensor take place over the wired modem 62. Sensors do not need to be connected via wires to the communications module if the communications module (and sensors) are operating in the wireless communication mode.

Of course, there may also be a hybrid communication mode in which both the wireless transceiver and the wired modem are active, so that communications with sensors take place both wirelessly and using wires. This may be used, for example, if each (wireless) sensor needs to use its own channel but there are fewer eligible channels than sensors required for a particular purposes, e.g. there is not enough time for all sensors on a single channel because of permanent part time interference of a TDMA system.

The communications module may be adapted to switch between the wireless communication mode and at least one other mode (e.g. the wired or non-communicative communication mode). Switching between the communication modes may comprise appropriate activation and/or deactivation of the wireless transceiver 61 and/or the wired modem 62 (if present).

In some embodiments, the wired modem (if present) is deactivated when operating in the wireless communication mode, to save energy. In some embodiments, the wireless transceiver is deactivated when operating in the wired communication mode, to save energy, or is used to monitor channels (e.g. by performing a claimed method).

Either the wireless signals 61A and/or the wired signals 62A may form the monitoring signals that provide monitored patient parameters to the communications module, depending upon the communication mode of the communications module and/or sensor(s).

The wireless transceiver 61 may be formed from one or more separate sub-transceivers (e.g. each designed for communicating using a different wireless communication protocol and/or with a different sensor and/or a separate sub-transceiver designed to permanently monitor the channels, and thereby not communicate with a sensor).

The communications module 60 also comprises a processing system 63 adapted to: determine a first noise value for each of a plurality of channels in which the at least one sensor and the communications module, when operating in a wireless communication mode, are able to communicate; determine the number of wireless communication channels having the first noise value below a predetermined threshold; and recommend whether or not a wireless communication mode is used based on the determined number of wireless communication channels.

In particular, the processing system 63 may be adapted to perform any previously described method. Of course, the processing system 63 may be further adapted to select or deselect the recommended communication mode and control its operation so as to communicate with the sensors via the wireless transceiver 61, or optionally the wired modem 62, based upon the selected communication mode, as would be apparent to the skilled person.

The processing system 63 may be adapted to communicate with a memory system 64, preferably formed of non-volatile memory such as flash memory. The memory system 64 may store calculated values of the channel and/or historic information (such as historic noise values) of the channel for processing by the processing system.

The communications module 60 may further comprise a power supply 65 for providing power to other components of the communications module 60, e.g. by converting a mains supply.

Of course, the communications module 60 may further comprise a user interface (not shown), such as a switch or button adapted to enable a user to switch the communications module between different power modes, e.g. ON, OFF, stand-by and so on. The processing system 63 may receive the user input and switch mode accordingly.

The user interface may also be adapted to enable a user to switch the communications module between different communication modes, e.g. between a wired and wireless communication mode. This may be performed by a user in response to a recommended communication mode.

In preferable embodiments, the communications module 60 comprises one or more battery chargers 66 adapted to connect to a sensor for charging the sensors. Thus, sensors may be "docked" into the communications module 60 for charging.

In some preferred embodiments, the communications module is adapted to only perform the step of determining a first noise value (and optionally the second noise value) for each of the plurality of channels when the communications module is not in wireless communication with any sensors, e.g. when the sensors are docked (if this functionality is present) or the communications module is switched to a standby or non-communicative mode. During this time, the processing system 63 may sequentially tune the wireless transceiver 61 to each known channel for measuring the first noise value (and optionally second noise value) of each channel. This measured information may be stored in the memory system 64 for later processing. This effectively build up a representative image of the availably and usage of each channel.

One limiting factor could be the availability of the wireless transceiver. In particular examples, the wireless transceiver may only be able to obtain the first noise value for each channel if the wireless transceiver is idle (i.e. not being used to communicate with a sensor). The wireless transceiver may be idle when all sensors belonging to the subject monitoring system are docked for charging or the communications module is switched to stand-by. When a transceiver is active (i.e. in communication with the sensors), the transceiver may switch between a receiving and transmitting mode, making the scanning and collecting of noise value(s) either impossible or extremely slow.

In further embodiments, the communications module 60 may be adapted to use sensors docked to the communications module for charging (if this functionality is present) to speed up the scanning cycle. Since the sensors typically have a radio unit which is comparable to (or at least compatible with) the wireless transceiver 61 used in the communications module 60, sensors docked for charging can be used for collecting channel data. Depending on the number of docked transducers the parallel scanning with multiple transducers speeds up the scanning cycle significantly.

In other words, the method of determining a first noise value for each of a plurality of channels may comprise using one or more sensors of the subject monitoring system to perform the determining of the first noise values. This may significantly increase the speed at which data of each channel is obtained.

Of course, reference to a "first noise value" in the description of the communications module may be expanded to refer to any information about a channel obtained by the communications module performing a claimed method, such as a second noise value. Thus, for example, docked sensors may be used to obtain a first and/or second noise value of each channel.

The wired modem 62 may be further adapted to communicate with a patient monitor (not shown). The processing system 63 of the communications module may receive signals 61A, 62A, containing monitored patient parameters, from sensors (via either the wireless transceiver 61 or the wired modem 62, depending upon the communication mode) and pass signals 62B containing the monitored patient parameter to the patient monitor (e.g. for storage and/or display) via the wired modem.

In other embodiments, the communications module 60 is integrated into a patient monitor, so that the processing system does not need to pass on signals received from the sensor. Rather, the processing system may itself process the signals received from the sensor, e.g. for storage and/or display.

In some embodiments, the communications module 60 comprises a display 67 or other user output (such as a speaker or haptic output) for indicating the recommended communication mode to the subject. In other embodiments, the communications module may pass a recommended communication mode to the patient monitor (not shown), which may provide the user output to the user (e.g. via a display of the patient monitor). Other methods of alerting a subject to a recommended communication mode will be readily apparent to the skilled person.

Embodiments of the invention extend to a subject monitoring system comprising the communications module herein described and one or more sensors, for monitoring a subject, able to communicate with the communications module in both a wired and wireless communication mode. In preferred embodiments, the communications module is adapted to charge the one or more sensors (e.g. using a dock) and the one or more sensors are corresponding adapted to be charged by the communications module (e.g. adapted to be docked into a dock of the communications module). The subject monitoring system may comprise one or more wires for connecting the respective one or more sensors to the communications module to enable wired communication, depending upon the recommended communication mode.

The skilled person would be readily capable of developing a processing system for carrying out any herein described method. Thus, each step of the flow chart may represent a different action performed by a processing system, and may be performed by a respective module of the processing system. The processing system may be integrated into a communications module of a subject monitoring system.

Embodiments may therefore make use of a processing system. The processing system can be implemented in numerous ways, with software and/or hardware, to perform the various functions required. A processor is one example of a processing system which employs one or more microprocessors that may be programmed using software to perform the required functions. A processing system may however be implemented with or without employing a processor, and also may be implemented as a combination of dedicated hardware to perform some functions and a processor (e.g., one or more programmed microprocessors and associated circuitry) to perform other functions.

Examples of processing system components that may be employed in various embodiments of the present disclosure include, but are not limited to, conventional microprocessors, application specific integrated circuits (ASICs), and field-programmable gate arrays (FPGAs).

In various implementations, a processor or processing system may be associated with one or more storage media such as volatile and non-volatile computer memory such as RAM, PROM, EPROM, and EEPROM. The storage media may be encoded with one or more programs that, when executed on one or more processors and/or processing systems, perform the required functions. Various storage media may be fixed within a processor or processing system or may be transportable, such that the one or more programs stored thereon can be loaded into a processor or processing system.

It will be understood that disclosed methods are preferably computer-implemented methods. As such, there is also proposed the concept of computer program comprising code means for implementing any described method when said program is run on a processing system, such as a computer. Thus, different portions, lines or blocks of code of a computer program according to an embodiment may be executed by a processing system or computer to perform any herein described method. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

Embodiments of the invention have been described with reference to channels. A channel is a range of frequencies that exists within a frequency band defined by the wireless protocol in use, e.g. Zigbee® typically defines 16 channels. In some embodiments, a channel may include one or more sub-channels (e.g. each covering a different sub-range of frequencies within a channel). In some embodiments, each sub-channel may be used by a sensor to communicate with the subject-monitoring signal. Thus, a noise value for a plurality of sub-channels may be obtained simultaneously. In embodiments, each channel may be represented by a (predetermined) frequency range, which frequency range may depend upon the wireless protocol in use.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". The term "patient" and the term "subject" have been used interchangeably throughout this document. Any reference signs in the claims should not be construed as limiting the scope.

The invention claimed is:

1. A method of recommending whether or not a subject monitoring system should use a wireless communication mode to communicate data between at least one sensor and a communications module of the subject monitoring system, the method comprising:
   determining, at the communications module, a first noise value for each of a plurality of channels in which the at least one sensor and the communications module, when the subject monitoring system operates in a wireless communication mode, are able to communicate;
   determining a number of eligible channels for wireless communication having the first noise value below a first predetermined threshold; and
   recommending whether or not a wireless communication mode should be used based on the determined number of eligible channels,
   wherein the step of recommending whether or not a wireless communication mode should be used comprises:
   in response to the number of eligible channels being above a second predetermined number:
      determining whether or not there are at least three adjacent eligible channels;
      in response to determining that there are at least three adjacent eligible channels, recommending that a wireless communication mode is used; and
      in response to determining that there are not at least three adjacent eligible channels, either:
         recommending that a wireless communication mode can be used, but may be unreliable; or
         recommending that a wireless communication mode is not used.

2. The method of claim 1, wherein the first noise value comprises a received signal strength indicator, RSSI, value.

3. The method of claim 2, wherein the first noise value comprises an average RSSI value, preferably obtained over a period of at least 30 minutes.

4. The method of claim 1, wherein the step of recommending whether or not a wireless communication mode should be used comprises:
   recommending that a wireless communication mode is not used when the number of eligible channels is below a first predetermined number; and
   recommending that a wireless communication mode is used when the number of eligible channels is above or equal to the first predetermined number.

5. The method of claim 1, wherein the step of recommending whether or not a wireless communication mode should be used comprises:
   in response to the number of eligible channels being at or below the second predetermined number:
      recommending that a wireless communication mode is not used when the number of eligible channels is below a first predetermined number; and
      recommending that a wireless communication mode can be used, but may be unreliable, when the number of eligible channels is above or equal to the first predetermined number.

6. The method of claim 1, wherein the step of, in response to determining that there are at least three adjacent eligible channels, recommending that a wireless communication mode is used comprises:
   recommending that a wireless communication mode be used in which a wireless communication takes place over an eligible channel, disposed directly between two other eligible channels.

7. The method of claim 1, further comprising determining, at the communications module, a time occupied value for each of the plurality of channels, the time occupied value being a length of time for which a second noise value of a respective channel is above a second predetermined threshold,
   wherein the step of determining the number of eligible channels for wireless communication comprises determining the number of eligible channels having the first noise value below the first predetermined threshold and the time occupied value below a third predetermined threshold.

8. The method of claim 7, wherein the first noise value is an average received signal strength indicator, RSSI, value and the second noise values is a received signal strength indicator, RSSI, value.

9. The method of claim 1, wherein the step of determining, at the communications module, a first noise value for each of a plurality of channels is performed only when the communications module is not in wireless communication with the at least one sensor.

10. The method of selecting a communication mode to be used by a subject monitoring system for communicating between at least one sensor and a communications module, the method comprising:
    recommending whether or not a wireless communication mode should be used by performing the method of claim 1; and
    selecting the wireless communication mode when it is recommended to use the wireless communication mode.

11. A communications module for a subject monitoring system, the communications module being operable to communicate with at least one sensor when the subject monitoring system operates in a wireless communication mode, the communications module comprising a processor adapted to execute code stored on a non-volatile computer memory to:
  determine a first noise value for each of a plurality of channels in which the at least one sensor and the communications module, when operating in a wireless communication mode, are able to communicate;
  determine a number of wireless communication channels having the first noise value below a predetermined threshold; and
  recommend whether or not a wireless communication mode is used by the subject monitoring system based on the determined number of wireless communication channels,
  wherein when the communications module recommends whether or not a wireless communication mode should be used, in response to the number of eligible channels being above a second predetermined number, the code further causes the processor to:
    determine whether or not there are at least three adjacent eligible channels;
    in response to determining that there are at least three adjacent eligible channels, recommend that a wireless communication mode is used; and
    in response to determining that there are not at least three adjacent eligible channels, either:
      recommend that a wireless communication mode can be used, but may be unreliable; or
      recommend that a wireless communication mode is not used.

12. The communications module of claim 11, wherein the code further causes the processor to determine the first noise value of each of the plurality of channels only when the communications module is not in wireless communication with the at least one sensor.

13. A subject monitoring system comprising:
  the communications module of claim 11; and
  one or more sensors, for monitoring a subject, the one or more sensors adapted to wirelessly communicate with the communications module when the subject monitoring system operates in a wireless communication mode.

14. The communications module of claim 11, wherein the first noise value comprises a received signal strength indicator, RSSI, value.

15. The communications module of claim 14, wherein the first noise value comprises an average RSSI value, preferably obtained over a period of at least 30 minutes.

16. The communications module of claim 11, wherein when the communications module recommends whether or not a wireless communication mode should be used, the code further causes the processor to:
  recommend that a wireless communication mode is not used when the number of eligible channels is below a first predetermined number; and
  recommend that a wireless communication mode is used when the number of eligible channels is above or equal to the first predetermined number.

17. The communication module of claim 11, wherein the step of when the communications module recommends whether or not a wireless communication mode should be used, in response to the number of eligible channels being at or below the second predetermined number, the code causes the processor to:
  recommend that a wireless communication mode is not used when the number of eligible channels is below a first predetermined number; and
  recommend that a wireless communication mode can be used, but may be unreliable, when the number of eligible channels is above or equal to the first predetermined number.

18. The communications module of claim 17, wherein in response to determining that there are at least three adjacent eligible channels, the code further causes processor to recommend that a wireless communication mode be used in which a wireless communication takes place over an eligible channel, disposed directly between two other eligible channels.

* * * * *